(12) United States Patent
Begg et al.

(10) Patent No.: US 10,556,050 B2
(45) Date of Patent: Feb. 11, 2020

(54) LOW COST VENTRICULAR DEVICE AND SYSTEM THEREOF

(71) Applicants: John Begg, Fitzroy Falls (AU); Komarakshi Rajagopalan Balakrishnan, Chennai (IN); Thorvascular Pty Ltd, Frenchs Forest (AU)

(72) Inventors: John Begg, Fitzroy Falls (AU); Peter Ayre, Frenchs Forest (AU); Komarakshi Rajagopalan Balakrishnan, Chennai (IN)

(73) Assignee: Thorvascular Pty Ltd, Frenchs Forest (AU)

(*) Notice: Subject to any disclaimer, the term of this patent is extended or adjusted under 35 U.S.C. 154(b) by 370 days.

(21) Appl. No.: 15/324,157

(22) PCT Filed: Jul. 9, 2015

(86) PCT No.: PCT/AU2015/000402
§ 371 (c)(1),
(2) Date: Jan. 5, 2017

(87) PCT Pub. No.: WO2016/004466
PCT Pub. Date: Jan. 14, 2016

(65) Prior Publication Data
US 2017/0157309 A1    Jun. 8, 2017

(30) Foreign Application Priority Data

Jul. 10, 2014    (AU) ................. 2014902668

(51) Int. Cl.
*A61N 1/362*    (2006.01)
*A61M 1/12*    (2006.01)
(Continued)

(52) U.S. Cl.
CPC .......... *A61M 1/122* (2014.02); *A61M 1/1012* (2014.02); *A61M 1/1029* (2014.02);
(Continued)

(58) Field of Classification Search
CPC .... A61M 1/101; A61M 1/122; A61M 1/1029; A61M 1/1012; A61M 1/1013;
(Continued)

(56) References Cited

U.S. PATENT DOCUMENTS 5,947,703 A    9/1999 Nojiri et al.
6,158,984 A    12/2000 Cao et al.
(Continued)

FOREIGN PATENT DOCUMENTS

WO    0064509 A1    11/2000

OTHER PUBLICATIONS

Authorized Officer: Ariane Le Guen, "International Search Report and Written Opinion" issued in counterpart PCT Application No. PCT/AU2015/000402, dated Sep. 3, 2015.
(Continued)

*Primary Examiner* — Mallika D Fairchild
(74) *Attorney, Agent, or Firm* — Kaplan Breyer Schwarz, LLP

(57) ABSTRACT

A blood pump device comprising: a centrifugal blood pump having: a pump housing defining an inlet to receive blood and direct blood onto an impeller, the pump housing having a top bezel and a central column directed into the middle of a cavity within the pump housing; the impeller is adapted, in use, to rotate in the cavity around the central column and to be suspended on a pivot bearing mounted between the middle of the lower surface of the impeller and the middle of the upper surface of the central column; the impeller is stabilised, in use, by the rotation of blades generating a
(Continued)

centrifugal force acting on the blades in radial direction away from the central column.

17 Claims, 11 Drawing Sheets

(51) Int. Cl.
*F04D 29/24* (2006.01)
*A61M 1/10* (2006.01)
*F04D 1/00* (2006.01)
*F04D 25/06* (2006.01)
*F04D 29/02* (2006.01)
*F04D 29/42* (2006.01)

(52) U.S. Cl.
CPC ............... *F04D 1/00* (2013.01); *F04D 25/06* (2013.01); *F04D 29/026* (2013.01); *F04D 29/242* (2013.01); *F04D 29/426* (2013.01); *A61M 2205/02* (2013.01)

(58) Field of Classification Search
CPC .............. A61M 1/1015; A61M 1/1036; A61M 1/1086; A61M 2205/3334; A61M 2205/02; F04D 29/026; F04D 29/426; F04D 29/048; F04D 29/242; F04D 25/06; F04D 1/00
See application file for complete search history.

(56) References Cited

U.S. PATENT DOCUMENTS

| | | | |
|---|---|---|---|
| 6,183,220 B1 | 2/2001 | Ohara et al. | |
| 6,609,883 B2 | 8/2003 | Woodard et al. | |
| 2003/0233021 A1 | 12/2003 | Nose et al. | |
| 2005/0196293 A1* | 9/2005 | Ayre | A61M 1/1015 417/353 |
| 2007/0270633 A1* | 11/2007 | Cook | H01J 37/32412 600/16 |
| 2011/0144413 A1* | 6/2011 | Foster | A61M 1/1017 600/16 |
| 2011/0218384 A1* | 9/2011 | Bachman | A61M 1/127 600/16 |

OTHER PUBLICATIONS

M. Yoshino et al., "Design and Evaluation of a Single-Pivot Supported Centrifugal Blood Pump", (/doi/10.1111.aor.2001.25.issue-9/issuetoc), "Artificial Organs", Jul. 7, 2008, pp. 683-687, vol. 25, Issue 9.

* cited by examiner

LOW COST VENTRICULAR DEVICE AND SYSTEM THEREOF

FIELD OF THE INVENTION

The present invention relates to a blood pump device that may be used as a ventricular assist device being suitable for left or right sides of heart preferably adapted to be able to be manufactured at a relatively low cost. The present invention may also include a ventricular assist system.

BACKGROUND OF THE INVENTION

Previously, there have been many attempts to create an improved heart assist device. Specifically, many of the previous inventions in this field have focused on providing a left ventricular assist device (LVAD) which is implantable.

Most of the devices and systems that have targeted the permanent implant market have focused on developing blood pumps that are suitable for beyond the general average life expectancy of the patient. This leads many implantable left ventricular assist devices (LVADs) to be over-engineered and being extremely expensive to manufacture.

Many of the LVADs used for permanent implantation are manufactured from stainless steel, nitinol, or titanium alloys. All of these exotic metals are relatively expensive to machine and difficult manufacture.

Additionally, there have been many previous inventions that target short term usage (typically less than 6 hours) and are typically not implantable. Also these inventions tend to be only suitable for applications during heart bypass operations or similar emergency situations. A majority of these types of devices are constructed of polymeric materials. A majority of these devices are designed to provide maximum pumping efficiency of the pumping fluid. However, many of these types of devices fail to reduce shearing forces on the pumping fluid. In LVADs, the pumping fluid is typically blood and wherein the LVAD imparts a relatively high shearing force on the blood, the blood tends to clot or haemolyse.

The previous short term devices typically result on patient complications or serious adverse events occurring for usage extending beyond about 8-12 hours. Also many of these short devices rotate at higher relative levels of rotations per minute (RPM) than the longer term devices and this may further exasperate the haemolysis effect.

U.S. Pat. No. 6,609,883—Woodard et al describes a blood pump fabricated mainly from Titanium-6 Aluminum-4 Vanadium (Ti-6A1-4V) coated with amorphous carbon and/or diamond-like coatings. In particular, the pump housing of this blood pump is metallic and includes a magnetic drive motor acting on a hydrodynamic impeller within the pump housing. One of the disadvantages with this invention is that as the pump housing is entirely constructed of metal, electrical eddy currents form between the motor stators and permanent magnets positioned within the impeller. These electrical eddy currents significantly reduce the electrical efficiency of the blood pump and may lead to increased power consumption.

Another U.S. Pat. No. 6,158,984—Cao et al describes a modified blood pump in which structural members are inserted within the pump housing between the motor stators and the impeller. These structural members are constructed of a biocompatible, corrosion resistant, electrically non-conductive (insulative) ceramic material. One of the disadvantages with the structural members being comprised of ceramic material is that ceramic material is relatively expensive and difficult to construct. The ceramic material may include a diamond like coating which may be particularly costly to produce and prone to flaking.

Another US Patent Application 20070270633—Cook et al describes a centrifugal blood pump with a hydrodynamically suspended polymeric impeller. This device includes an impeller of a difficult manufacturing shape with dimensional stability issues relating to the tights tolerances of the impeller blades in relation to the housing. Minor dimension changes in use or in moulding of this invention may possibly lead to pump stop or clotting issues.

It has been previous known to this field, that rotary blood pumps may be entirely constructed from polymeric material except for the motor components. However, pumps that are entirely constructed of polymeric materials may lack the desired: wear resistance or strength, fluid impermeability and bio-resistance necessary for this type of application. These types of pumps commonly warp or distort due to fluid absorption limiting their usefulness.

Any discussion of the prior art throughout the specification should in no way be considered as an admission that such prior art is widely known or forms part of common general knowledge in the field.

SUMMARY OF THE INVENTION

Problems to be Solved

It is an object of the present invention to provide a generally low cost or easier to manufacture LVAD wherein the risk of haemolysis or blood clotting is relatively reduced or minimised.

It is an object of the present invention to overcome or ameliorate at least one of the disadvantages of the prior art, or to provide a useful alternative.

Means for Solving the Problem

A first aspect of the present invention may relate to a blood pump device comprising: a centrifugal blood pump having: a pump housing defining an inlet to receive blood and direct blood onto an impeller, the pump housing having a top bezel and a central column directed into the middle of a cavity within the pump housing; the impeller is adapted, in use, to rotate in the cavity around the central column and to be suspended on a pivot bearing mounted between the middle of the lower surface of the impeller and the middle of the upper surface of the central column; the impeller is stabilised, in use, by the rotation of blades generating a centrifugal force acting on the blades in radial direction away from the central column.

Preferably, the impeller includes a plurality of blades extending radially away from a centre of the impeller, the blades to force blood received at the inlet through the pump housing and to the outlet. All of the blades may be preferably joined about a central pivot mount and wherein each blade is joined to an adjacent blade with an elongated arm.

A preferred drive unit is attached and secured against an outer lower surface of the pump housing and wherein a protrusion from the upper surface of the drive unit engages with respective recess in the outer lower surface of the pump housing.

Additionally, the preferred drive unit may house an electrical motor connected to elongated pivot member, wherein the pivot member is adapted to spin within the protrusion when electrical current is applied to the electrical motor.

Preferably, the elongated pivot member includes a plurality of first set of permanent magnets mounted along the length of the pivot member which are adapted to engage a second set of permanent magnets positioned within the blades so as to allow the blades to rotate when the pivot member is rotated by the electrical motor.

Preferably, the pump housing is integrally moulded from a polymeric substance and the impeller may be integrally moulded from a polymeric substance.

A second aspect of the present invention may relate to an implantable blood pump system comprising: a centrifugal blood pump having: a pump housing defining an inlet to receive blood and direct blood onto an impeller, the pump housing having a top bezel and a central column directed into the middle of a cavity within the pump housing; the impeller is adapted, in use, to rotate in the cavity around the central column and to be suspended on a pivot bearing mounted between the middle of the lower surface of the impeller and the middle of the upper surface of the central column; the impeller is stabilised, in use, by the rotation of blades generating a centrifugal force acting on the blades in radial direction away from the central column.

A third aspect of the present invention may relate to a blood pump device comprising: a centrifugal blood pump having: a pump housing defining an inlet to receive blood and direct blood onto an impeller, the pump housing having a top bezel; the impeller is adapted, in use, to rotate in the cavity and to be suspended on a pivot bearing mounted between the middle of the lower surface of the impeller and the impeller includes at least three blades joined to a central hub wherein the blades include an upper region 41 and a lower region 42 and wherein the lower region of each blade extends generally upwardly in a vertical direction and the upper region of each blade is deflected from the vertical axis by an angle in a direction opposed to rotation of the impeller in use.

Preferably, wherein the angle is between 1 to 90 degrees. More preferably, the angle is between 10 to 45 degrees.

Each blade may be arcuate when in viewed from a top or bottom view.

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

DETAILED DESCRIPTION

Preferred embodiments of the invention will now be described with reference to the accompanying drawings and non-limiting examples.

Figure 1:
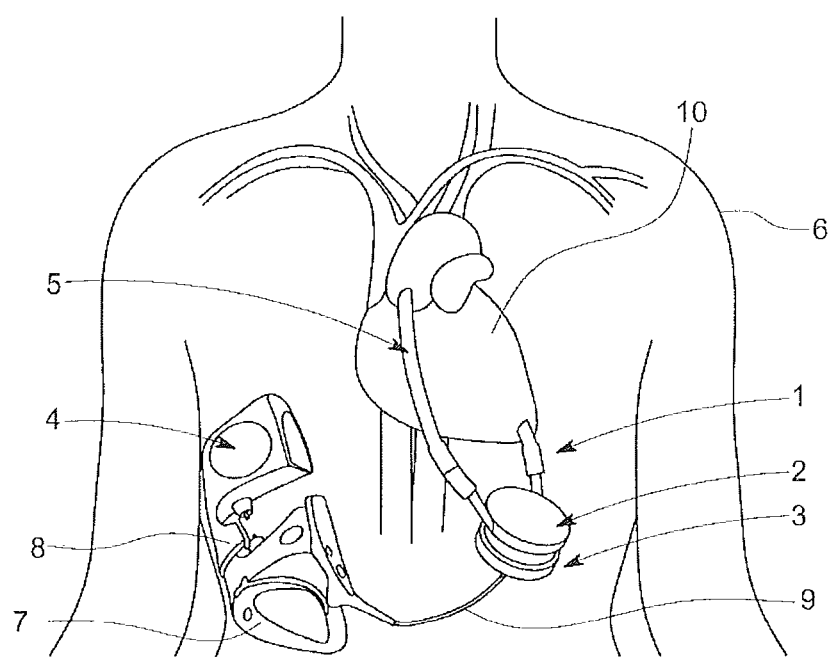
FIG. 1 depicts a schematic illustration of a first preferred embodiment of the present invention wherein the embodiment is in use.
Figure 2:
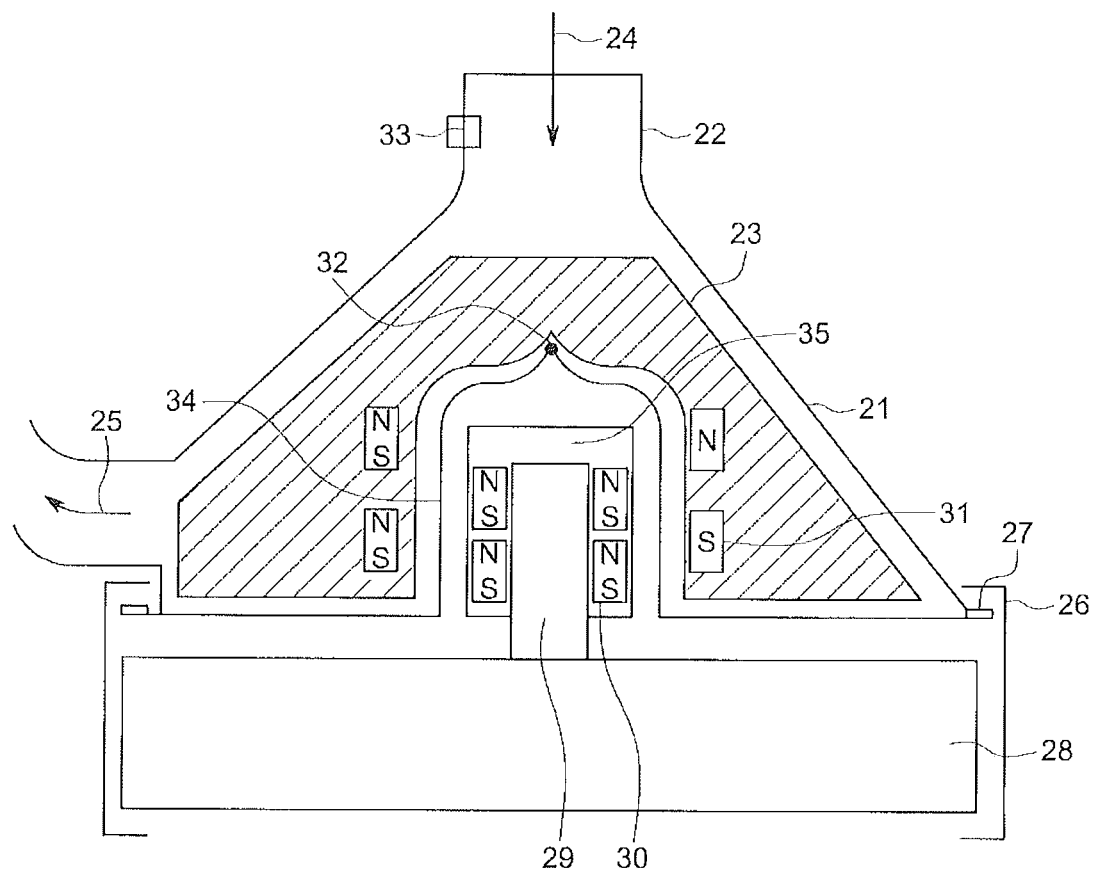
FIG. 2 depicts a cross sectional side view of a portion of the first preferred embodiment including a blood pump and drive unit.
Figure 3:
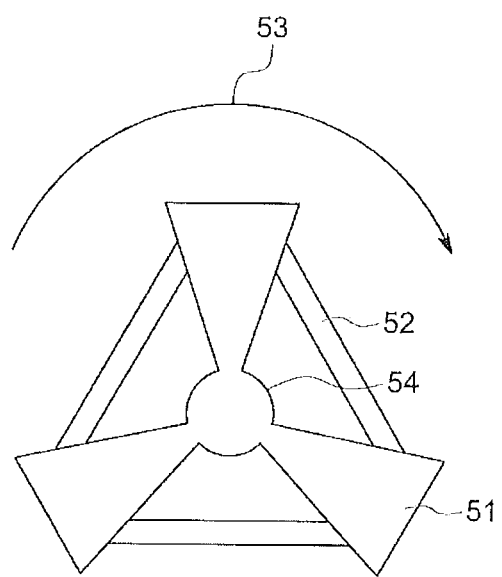
FIG. 3 depicts a top view of an impeller adapted to be used within the blood pump of the first preferred embodiment.
Figure 4:
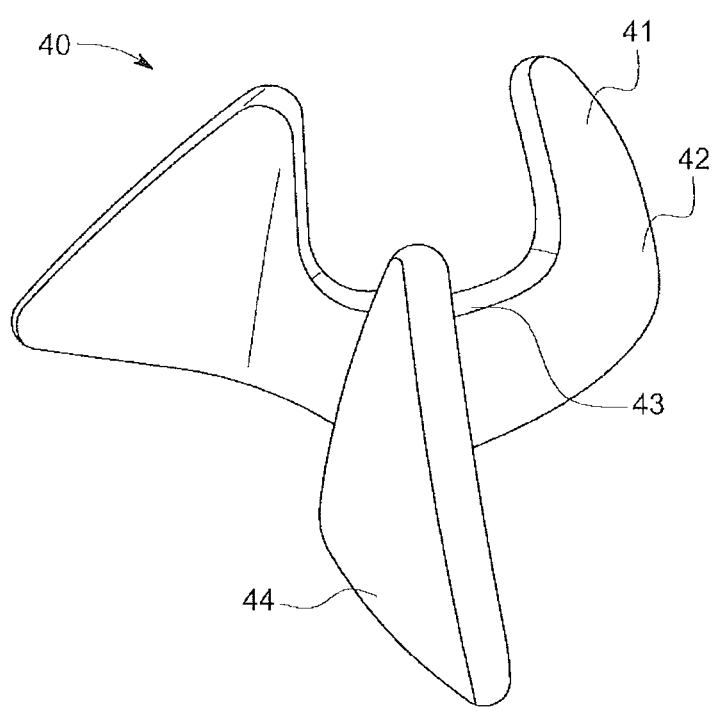
FIG. 4 depicts a front perspective view of an impeller adapted to be used with a second preferred embodiment of the present invention.

A first preferred embodiment of the present invention is depicted in FIGS. 1-3. Preferably, a Ventricular Assist Device (VAD) or Ventricular Assist System (VAS) is provided and includes a centrifugal blood pump which further includes an inlet 22 and outlet 25.

Preferably, the pump is magnetically driven to rotate preferably clockwise (when viewed from the top view. In FIG. 3, the impeller 23 is shown to be rotating clockwise as depicted by direction 53. The pump includes a pump housing 21 having an upper and lower portion and an internal cavity. Preferably, an impeller 23 is positioned within the cavity and is adapted to rotate within the cavity. When the impeller 23 rotates it imparts a centrifugal force on the blood which occupies the cavity when in use.

The blood is forced or pushed in a radial direction away from the centre of the pump housing towards an outer wall of the pump housing. As the blood rotates, it eventually exits the pump housing through the outlet 25. Thereby the rotation of the impeller 23 pushes the blood from the inlet 24 the outlet 25. Centrifugal blood pumps of this configuration may generally reduce shearing forces on the blood.

Preferably, the diameter of the lower portion of the pump housing is within a range of 25-40 cm. Also the diameter of the impeller 23 mimics a similar diameter to the lower portion of the housing is generally about 2-5 cm less in diameter. This sizing may produce optimal pumping conditions wherein the impeller RPM is not too high to cause significant levels of blood damage. Smaller diameter pump may lead to inverse increases in impeller RPM causing increased risk of haemolysis.

The outer surface of the lower portion of the pump housing preferably including a protrusion 34 which is directed towards the centre of the cavity. This protrusion 34 may form a central column about which the impeller may spins. Preferably the impeller includes a recess adapted to receive the central column. Preferably, on the uppermost tip or central point of the central column is positioned or mounted a pivot bearing 32 which in turn engages the middle of the lower surface of the impeller.

When in use, the impeller rotates about the central column, the pivot bearing 32 is mounted in the middle or centre of the uppermost point of the central column and is preferably constructed of a low wear resilient and biocompatible material such as titanium alloy, stainless steel or ceramic. Preferably, the pivot bearing 32 is in the form of a single ball bearing, the cost of manufacture of this component is relatively low cost to manufacture. The act of rotation of the impeller imparts a stabilisation force on the impeller 23 wherein the impeller experiences forces 90 degrees to axis of rotation and wherein this stabilisation force is relatively constant around the outer circumference of the impeller.

Preferably, the impeller is constructed from polymeric materials that are biocompatible and resist to fluid ingress. Constructions materials may include PEEK, polycarbonate (PC) or polyurethane (PU). Preferably, the impeller may include magnets mounted or positioned within the blades.

Preferably, the impeller 23 as depicted in FIG. 3 includes three blades 51 extending radially from a central connection point 54. The blades each respectively have a general triangular profile or wedge shape profile when viewed from the top view. The number of blades may be varied so long as the impeller remains balanced when in use or rotation.

Each blade 51 is preferably connected to its neighbouring respective blade by an arm or bridge 52. Preferably, the impeller when viewed from the top view in FIG. 3 has an overall triangular appearance when three blades are utilised in the design. However other variations could possibly include four blades forming square shaped impeller or five blades forming a pentagon shaped impeller. Three blades are preferred in the preferred embodiment as gives the impeller good stability when rotated and the numbers of edges from the blades is generally minimised, which may lead to reduction in blood clotting or haemolysis.

The impeller 23 is preferably driven to rotate by the interaction and cooperation of sets of magnets. Preferably, a drive unit 28 includes an electrically actuated motor (which may preferably be a DC brushless motor) mechanically connected to an elongated pivot member 29. The elongated pivot member 29 is integrally formed to the shaft of the motor within the drive unit 28. The elongated pivot member 29 may include a first set of permanent magnets 30 mounted, positioned or integrally moulded to the outer surface of the elongated pivot member 29. Wherein the motor is actuated, the shaft and elongated pivot member 29 is also rotated in the desire direction.

A second set of permanent magnets 31 are to be mounted, positioned or integrally moulded in the corresponding proximal surfaces of the blades 51 in the impeller 23. The second set of permanent magnets is adapted to magnetically engage with the respective magnets forming the first set 30. When the first set of magnets 30 are rotated by the motor, the second set of magnets 31 will transfer torsional force to the blades and rotate the impeller.

Further, the attractive forces between the first and second sets of magnets are adapted to apply a subtle downward pressure (relative to the side view shown in FIG. 2) or bias on the impeller to make sure that the impeller does not lift off from the pivot bearing. This may form a limited magnetic restraint in the movement of the impeller in the vertical direction away from the lower portion of the pump housing. Thereby, the impeller is preferably suspended in the cavity by a combination of magnetic force, pivot bearing applying a physical force upwards and the centrifugal force of the blades, when in use.

Preferably, the pump housing and the impeller are constructed of polymeric materials except for the drive unit 28 and the sets of permanent magnets. Preferably, the permanent magnets are constructed of rare earth magnets and these magnets may be coated and encapsulated with an impermeable substance to prevent fluid ingress or corrosion of the magnets. Alternately, the polymer or plastic magnets may be used as permanent magnets. These polymer magnets are non-metallic magnet and resistant to corrosion and made from organic polymer. An example of a suitable organic polymer may be PANiCNQ which is a combination of emeraldine-based polyaniline (PNAi) and tetracyanoquinodimethane (TCNQ).

Preferably, the pump housing 21 includes a tongue 27 extending from the lower portion of the pump housing in a radial direction away from the centre of the pump housing. The tongue 27 is adapted to mate or be secured with a clip 26 which joins and secures the drive unit 28 to the pump housing 21. Preferably, the clip is adapted to engage the lower portion of the pump housing and at least a portion of the drive unit 28. In FIG. 2, the clip has engaged the lower most outer surface of the drive unit and acts to clamp the drive unit in place against the lower surface of pump housing. The clip 26 may be resilient and flexible and able to be engaged or disengaged with appropriate hand pressure. The clip may extend around the full circumference of the pump housing or alternately be secured just on opposite sides of the pump housing using two relatively small clips as shown in FIG. 2.

Preferably, the upper portion of the pump housing 21 may form a sloping bezel wherein the upper surface of pump housing is generally conical shaped. The impeller may generally include the same or similar conical shape or profile on its upper surface.

Preferably, a pressure sensor 33 may be mounted or positioned on the inner wall of the inlet 22. When in use, blood flows in the direction 24 past the pressure sensor 33 and an electrical signal is generated by the sensor 33 which may be feedback to a controller which regulates the speed and action of the pump. Additionally, information from the pressure sensor may logged and recorded by a controller and supplied to a clinician or physician as the necessary review times.

The preferred system forming part of the first preferred embodiment is depicted in FIG. 1. In this figure, a patient 6 has been implanted with the preferred system and device and the system or device is adapted to allow a VAD to be connected to the heart 10. The pump housing shown as 1 has been attached and secured to the drive unit 3. An inflow cannula connects the apex of the left ventricle to the inlet of the pump housing and allows for blood to be pumped from a cored aperture in the apex of the left ventricle into the ascending aorta. The outlet of the pump housing 2 is connected to an outflow cannula 5 which is secured and in fluid communication with the ascending aorta.

Preferably, the drive unit 3 is electrically attached to a controller 7 by a set of wires 9 adapted to commutation control to the motor of the drive unit 3. The controller 7 includes a quick release lever and a socket 8 which cooperate to engage and secure a battery 4. In FIG. 1, an overmoulded battery 4 has been encapsulated in a polymeric housing. The battery 4 is adapted to be secured to the controller by a locking mechanism featured as socket 8. Preferably, the battery 4 may Li Ion or NiMH based.

Preferably, the controller 7 may control the speed of the blood pump by controlling the commutation speed of the motor. The speed may be automatically adjusted to suit the needs of the patient 6. The controller may also regulate the pump speed in a pulsatile manner. Alternately, the pump speed may set by a physician and regulated at a suitable level based on feedback from a pressure sensor in the blood pump.

The described system may be partially or fully implantable depending on the circumstances and needs of the patient. The system may also be used to assist the right or left sides of heart. Wherein the system is attached to the right side, the pumping speed is generally lower than that of left side application. FIG. 1 only depicts the left side application but a person skilled in the art may adapt the system for right side applications.

The following polymeric substances are examples of materials from which the embodiments may be constructed.

Polyetheretherketone ('PEEK')

An example of a polymeric material that may be used in the constructions of an embodiment is PEEK. It has a relatively high thermal stability compared with other thermoplastics. It typically retains high strength at elevated temperatures, and has excellent chemical resistance (being essentially inert to organics, and has a high degree of acid and alkali resistance). It has excellent hydrolytic stability and gamma radiation resistance. Therefore PEEK may be readily sterilised by different routes. It also shows good resistance to environmental stress cracking. It generally has excellent wear and abrasion resistance and a low coefficient of friction PEEK may incorporate glass and/or carbon fibre reinforcements which may enhance the mechanical and/or thermal properties of the PEEK material.

PEEK may be easily processed on conventional extrusion and injection moulding equipment. Post-annealing and other processes obvious to a person skilled in the art may be preferable. A polyaromatic, semicrystalline polymer may also be used in construction of an embodiment.

Other examples of this polymer include: Polyaryletherketone ('PAEK') manufactured by Victrex and PEEK-OPTINMA LT™ which is a polymer grade with properties optimised for long-term implants. PEEK-OPTIMA LT™ is significantly stronger than traditional plastics currently available. Generally, PEEK may be able to withstand more aggressive environments and maintain impact properties over a broader range of temperatures than other polymers.

It has been shown that carbon fibre reinforced PEEK found to exhibit excellent resistance to a saline environment at 37° C. designed to simulate human body conditions.

PEEK includes the significant advantage of generally supplying dimensional stability, when in use.

Fibre Reinforced Polymer ('FRP')

Another example of a polymeric material that may be included within an embodiment of the present invention is FRP. FRPs are constructed of composites of PEEK and other polymers. PEEK may be reinforced with 30% short carbon fibres and which when subjected to saline soaking, was found to exhibit no degradation in mechanical properties. In contrast, a 30% short carbon fibre reinforced polysulphone composite has been found to show degraded mechanical properties due to the same saline soaking.

The fibre/matrix bond strength may significantly influence the mechanical behaviour of FRP composites. Interfacial bond strength durability is therefore particularly important in the development of FRP composites for implant applications, where diffused moisture may potentially weaken the material over time. Testing in physiologic saline at 37° C. showed that interfacial bond strengths in carbon fibre/polysulfone and carbon fibre/polyetheretherketone composites significantly decrease.

It should be noted that the fibre/matrix bond strength is known to strongly influence fracture behaviour of FRP composites.

Polycarbonate ('PC')

Another example of polymer material that may be used in the construction of the preferred embodiments are PC resins. PC resins are widely used where transparency and general toughness are sought.

PC resins are intrinsically amorphous due to the large bulky bis-phenol component. This means that the polymer has a significantly high free volume and coupled with the polar nature of the carbonate group, the polymer can be affected by organic liquids and by water. PC resins are not as resistant to extremes in pH as PEEK however they are at least partially resistant.

PC resins generally have very low levels of residual monomers and so PC resins may be suitable for blood pump construction. PC resins generally have desirable mechanical and thermal properties, hydrophobicity and good oxidative stability. PC resins are desirably used where high impact strength is an advantage. PC resins also generally confer good dimensional stability, reasonable rigidity and significant toughness, at temperatures less than 140° C.

PC resins may be processed by all thermoplastic processing methods. The most frequently used process is injection moulding. Please note that it may be necessary to keep all materials scrupulously dry due to small but not negligible moisture pick-up of this resin. The melt viscosity of the resin is very high, and so processing equipment should be rugged. Processing temps of PC resins are relatively high generally being between approximately 230° C. and 300° C.

Polysulphone ('PS')

Another example of a polymeric material that may be used to construct parts of an embodiment from is PS. PS has relatively good high temperature resistance, and rigidity. PC is generally tough but not notch-sensitive and is capable of use up to 140° C. It has excellent hydrolytic stability and is able to retain mechanical properties in hot and wet environments. PS is generally chemically inert.

PS is similar to PC resins but may be able to withstand more rigorous conditions of use. Additionally, PS is generally more heat resistant, and possesses a greater resistance to creep and better hydrolytic stability. PC has a high thermal stability generally due to bulky chemical side groups and rigid chemical main backbone chains. It is also generally resistant to most chemicals.

Injection moulding used for lower melt index grades, whilst extrusion and blow moulding is used to form components generally made of higher molecular weight PS.

Polyarethanes (PU)

Another example of a polymeric material that may be include within an embodiment of the present invention is PU. PU is one of the most biocompatible and haemocompatible polymeric materials. PU has the following properties: elastomeric characteristics; fatigue resistance; compliance and acceptance or tolerance in the body during healing; propensity for bulk and surface modification via hydrophilic/hydrophobic balance or by attachments of biologically active species such as anticoagulants or bio-recognisable groups. Bio-modification of PU may be possible through the use of a several antioxidants used in isolation or in combination. These antioxidants may include vitamin E, which may create materials which can endure in a patient's body for several years.

PU constitutes one of the few classes of polymers that include the properties of being generally highly elastomeric and biocompatible.

Polyether Polyurethanes ('PEPU')

Another polymeric material that may be used in the construction of an embodiment is PEPU. PEPU generally has: relatively good flexural performance and acceptable blood compatibility.

Polycarbonate Urethane ('PCU')

PCU may also provide another alternative polymeric material for the purpose of constructing an embodiment.

PCU has significantly lower rates of water transmission or impermeability. This is due to inherently lower chain mobility of the carbonate structure in the soft segment phase. Additional impermeability to water vapour can be achieved by selecting a polyurethane polymer with high hard segment content, and aromatic rather than aliphatic di-isocyanate co-monomer, and a more hydrophobic surface.

PCU generally has oxidative stability of the carbonate linkage, which reduces the rate of biodegradation tremendously as compared to the polyether polyurethanes.

Siloxane-Urethanes ('SiU')

SiU is another example of an alternative preferred polymeric material. SiU generally has a combination of properties including: fatigue strength, toughness, flexibility and low interaction with plasma proteins. However these polymers may be relatively soft.

Polyvinylchloride ('PVC')

PVC is another example of an alternative preferred polymeric material. PVC is a relatively amorphous and rigid polymer which in the absence of plasticiser has a glass transition around Tg 75° C.-105° C. It is a cheap tough polymer which is extensively used with many types of filler and other additives. Although it has a high melt viscosity and therefore in theory is difficult to process, specialised methods have been established for several decades to compound this polymer efficiently.

Extraction-resistant grades of PVC are required for long-term blood compatibility. Plasticised PVC has been well established for blood bags and similar devices, and resin manufacturers can keep toxic residual monomer levels acceptably low (<1 ppm). However there is enormous social pressure to outlaw PVC despite scientific data which generally indicates that PVC is benign.

Poly Vinylidene Fluoride ('PVDF')

PVDF is a polymer that possesses relatively good amounts of toughness and biocompatibility to be suitable for use in constructing an embodiment.

Polyethylene ('PE')

PE is available in several major grades, including Low Density PE ('IDPE'), High Density PE ('HDPE') and Ultra High Molecular Weight Grade PE ('UHMWPE'). However the UHMWPE may be likely to be the most suitable as it generally possesses relative toughness, low moisture absorption, and good overall chemical resistance.

Sintered and compression moulded UHMWPE has been well established for hip joints replacement. However further improvements appear necessary, as abrasive resistance and wear are not suitable for lengthy (>5-10 year) use. A major limitation of PE is thermal performance (melting point approximately 130° C.) and dimensional stability.

Polypropylene ('PP')

Another suitable polymeric material is PP. PP is a versatile polymer that may possess a combination of features including: relative inertness, relatively good strength and good thermal performance. Depending on the grade, Tg ranges from 0° C. to −20° C. and the MPt is approximately 170° C. The most common grades are homo- and ethylene copolymers, the latter with improved toughness.

In addition, there have been many advances in reactor technology leading to grades which are either much softer than normal or much stiffer. For example, the Bassell Adstiff™ polymers made using Catalloy™ technology may be suitable and/or include desirable features for use in the manufacture of a blood pump. Generally, PP polymers lack the high melting point of PEEK, but this property is not generally desired.

Polymethylmethacrylate (PMMA)

PMMA is an amorphous material with good resistance to dilute alkalis and other inorganic solutions, and has been shown to be one of the most biocompatible polymers. Therefore, PMMA may include some of the desirable features and may be used in the construction of an embodiment of the present invention. Generally, PMMA easily machined with conventional tools, moulded, surface coated and plasma etched.

PMMA's may be susceptible to environmental stress cracking although this is usually associated with the use of organic solvents, not present in a patient's body and a blood pump working environment.

Acrylonitrile-Butadiene-Styrene Terpolymers (ABS)

ABS generally has relatively good surface properties including: hardness, good dimensional stability and reasonable heat resistance (Tg approximately 120° C.). The combination of the three monomers imparts stiffness (styrene), toughness (butadiene) and chemical resistance (acrylonitrile).

Other attributes of ABS may include: rigidity, high tensile strength and excellent toughness as well as excellent dimensional accuracy in moulding. ABS is generally unaffected by water, inorganic solvents, alkalis; acids; and alcohols. However certain hydrocarbon solvents, not usually present within the body of a patient or in the working environment of the blood pump, may cause softening and swelling on prolonged contact.

Polyesters ('PET')

PET have become one of the largest growing thermoplastics over the past decade: volumes and prices are now approaching PE and PP. PET has a Tg around 75° C. and melting point of 275° C. It can vary from about 25% to 70% in crystallinity depending on the processing history of the polymer. Physical properties and chemical resistance are very dependent on crystallinity. PET may also have limited dimensional stability, as crystallisation can slowly increase after moulding. PET are generally tough, transparent, stiff and opaque.

Another class of PET with a Tg above 100° C. is currently available, this polymer is called Polyethylene Naphthenate ('PEN'). PET and PEN may both be suitable for use in the construction of a blood pump.

Polyamides and/or Nylons ('PA')

PAs and Nylons are characterised by having excellent wear/frictional properties, high tensile impact and flexural strength and stiffniess, good toughness and high melting points.

Some PAs may include relatively large hydrocarbon spacers between the amide groups. Examples of this type of PA include Nylon 11 and 12 which are generally more hydrophobic (water uptake <1%) than regular varieties of PAs. However the larger spacing leads to a loss in stiffness compared to the other polymers and thermal performance may also be compromised.

Fully aromatic polyamides including Kevlar™ and Nomexn5 are commercially available and have high stiffness and melting points. Semi-aromatic polyamides are made in Germany (eg Trogamid™ T) and France. These semi-aromatic polyamides generally have good transparency and chemical resistance.

Acetal Resins and/or Polyoxymethylene ('AR')

AR may be used to construct any one of the preferred embodiments. This class of polymer is strong, hard, and abrasion resistant. It has been evaluated for joint replacement components and other long-term implants.

The acetal homo-polymer is prone to salt induced cracking, but copolymers with small amounts of a propylene oxide are possible. AR which contains formaldehyde may be of concern due to possible toxicity of formaldehyde.

Polydimethylsiloxane ('PDSM')

PDSM may be used to construct any one of the preferred embodiments.

This polymer is generally elastomeric. It may also be considered for use as either a biocompatible coating or a copolymer.

Copolymers based on PDMS and PU have been developed and PDMS/PC are commercially offered by General Electric as Lexan™ 3200. The latter is a fairly stiff transparent material with excellent UV performance.

Syndiotactic Polystyrene ('SP')

SP may be used to construct any one of the preferred embodiments. SP is typically highly crystalline, little change in modulus occurs at the Tg of 100° C., and retention of properties is fairly high to the melting point of over 250° C. Many grades may be fibre reinforced, to filer reduce the change in modulus at the Tg. Being a hydrocarbon with no hetero atoms, the polymer may be hydrophobic and inert.

Aliphatic Ether Ketones ('AEK')

AEK may be used to construct any one of the preferred embodiments.

Processing and mechanical performance are similar, but this polymer shows improved high temperature aging behaviour and little notch sensitivity. Unfortunately the material lacked distinctiveness and is no longer produced.

TOPAS™ ('T')

T may be used to construct any one of the preferred embodiments. This class of co-polymer is made by Ticona in Germany. It generally comprises ethylene and norbomadene, with the Tg being controlled by monomer ratio. It is a hydrocarbon alternative to polycarbonate, and is generally suitable for medical fittings and devices. Its Tg is over approximately 130° C. and it is generally transparent with the co-monomer inhibiting crystallisation of the ethylene segments.

Metallocene PP ('MPP') MPP may be used to construct any one of the preferred embodiments MPP is manufactured by Exxon to compete with existing PP. It has a much narrower molecular weight distribution (polydispersity around 2) because it is oligomer-free.

Second and third embodiments of the present invention are depicted in FIGS. 4-11. In the second embodiment, an alternative impeller 40 has been provided. This impeller 40 is adapted to rotate in the direction 53 in FIG. 6. The impeller includes at least three blades 44 and preferably these blades are integrally moulded to a central connection point or hub 43.

Figure 6:
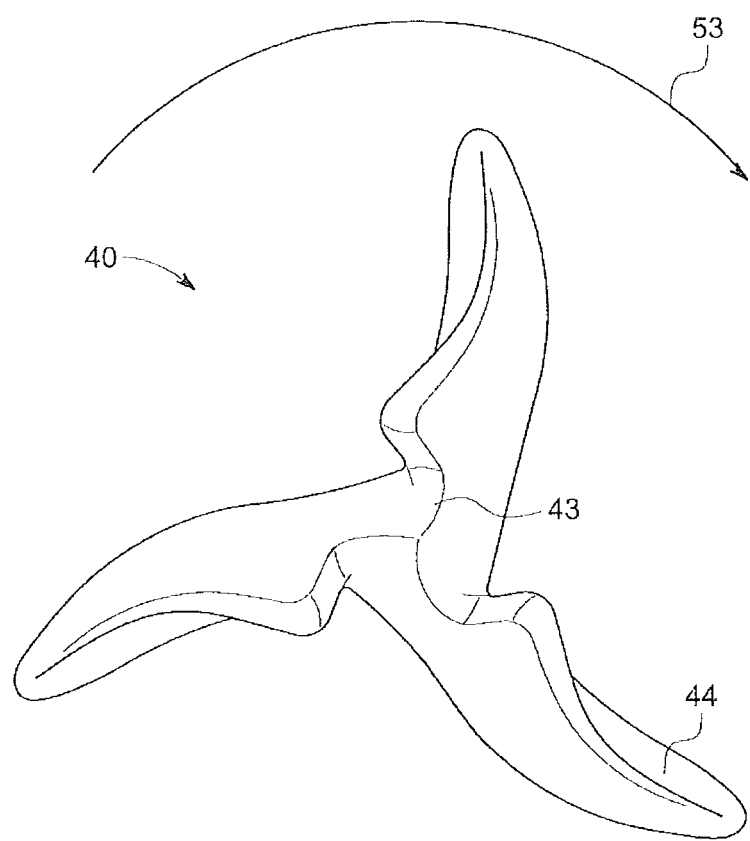
FIG. 6 depicts a top view of the impeller shown in FIG. 4.

The blades 44 include an upper region 41 and lower region 42 as determined by the top and bottom of the blood pump in which the impeller is mounted or positioned within. The lower region extends generally upwardly in a vertical direction and at about half of the height of the overall blade height, the upper region 41 begins. The upper region 41 is preferably deflected from the vertical axis by an angle of between 1 to 90 degrees. More preferably, the angle of deflection is between 10 to 45 degrees. Preferably, the deflection is in a direction opposed to the rotation direction 53 of the impeller as shown in FIG. 6.

Each of the blades 44 is preferably arcuate or curved when in viewed from a top or bottom view and includes a set of permanent magnets which functions to same mechanical manner to the second set of permanent magnets in the first preferred embodiment.

Preferably, the impeller 40 includes a valley or recess located or positioned between the blades 44 and the hub 43. Preferably, the recess is centred above the hub 43 so as to reduce the risk of haemolysis from slow or stagnant blood flow in the centre of the blood pump.

The outer edges of the blades 44 are adapted to conform to the shape of the inner wall or surface of the pump housing.

Figure 5:
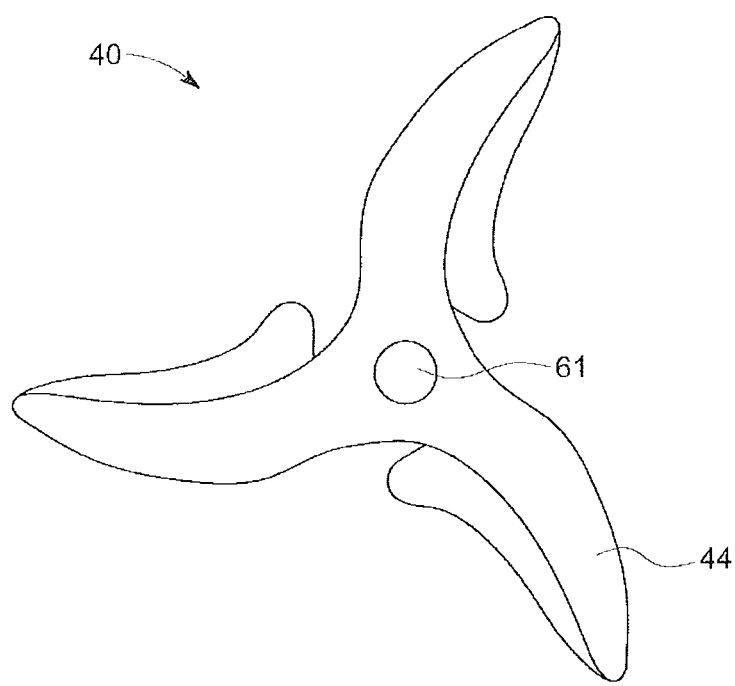
FIG. 5 depicts a bottom view of the impeller shown in FIG. 4.
Figure 7:
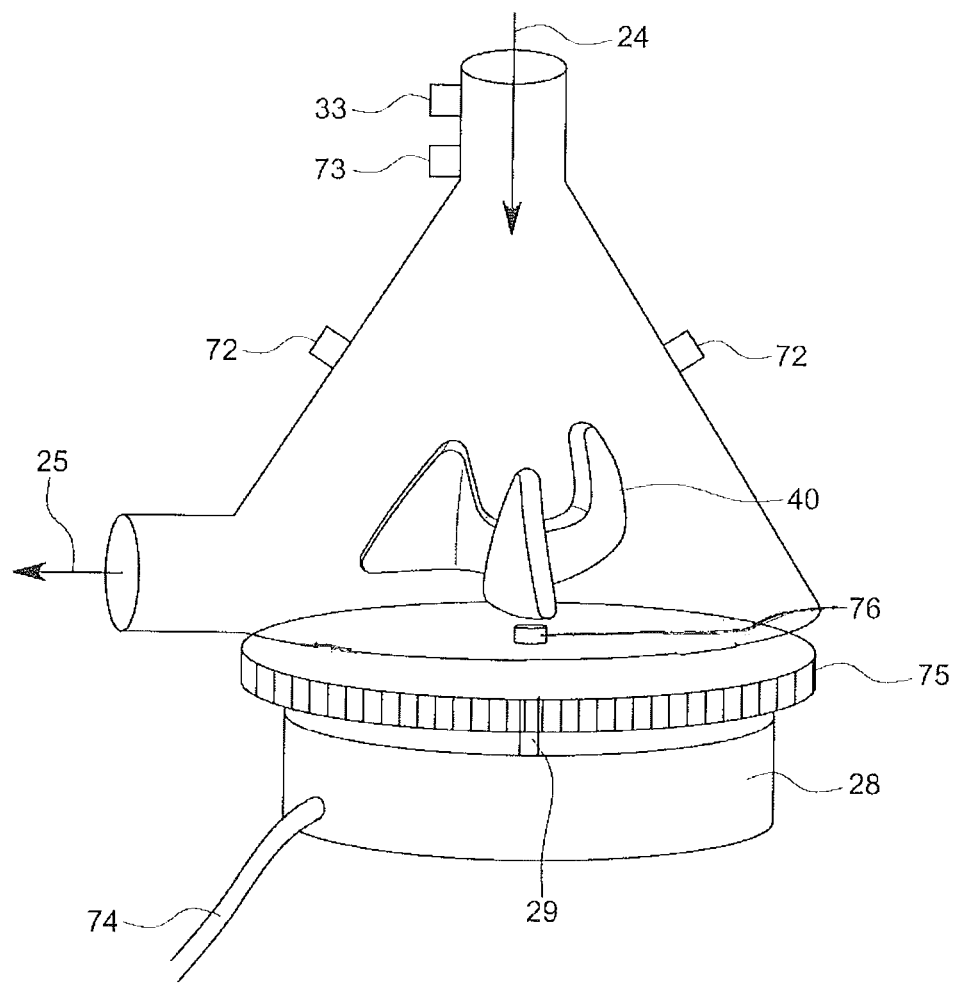
FIG. 7 depicts a cross sectional view of a blood pump according to the second preferred embodiment of the present invention.

FIG. 5, depicts a pivot bearing recess 61 mounted or positioned in the underside of the impeller 40, which is adapted to receive as relatively small pivot bearing mount 76 extending from the middle of the lower inner wall or surface of the blood pump as depicted in FIG. 7. The pivot bearing arrangement may include a ceramic or wear resistant pivot bearing to be mounted between point 76 and 61 to allow for the relatively free rotation of the impeller 40 within the housing.

FIG. 7 depicts a blood pump similar in construction to the first preferred embodiment shown in FIG. 2. However, the elongated pivot member 29 no longer protrudes into the middle of the blood pump but rather is attached to a flat rotatable disc 75. The disc 75 includes the first set of permanent magnets which are adapted to engage the second set of permanent magnets mounted in the blades 44. When the disc 75 is rotated, the impeller 40 is likewise rotated.

Rotation or torsional force is preferably applied by the drive unit 28 which includes a motor with a shaft. The shaft is attached to elongated pivot member 29 which is in turn joined the centre of the disc 75.

The electrical motor in the drive unit 28 is preferably powered by wires 74.

The blood pump shown in FIG. 7 has similar features to the blood pump depicted in FIG. 2. Similar labelling has been used to designate the same or similar components.

In this embodiment, a third set of permanent magnets 72 have been mounted or positioned in the upper region of the pump housing. This third set of magnets serve as biasing magnets to apply a biasing force onto the magnets in the impeller to minimise or prevent the impeller lifting off the pivot bearing, when in use.

Blood viscosity sensors 73 may also be included within the design and mounted or positioned in the inlet of the pump. Please note that these sensors may be integrally moulded into the polymeric pump housing.

Figure 8:
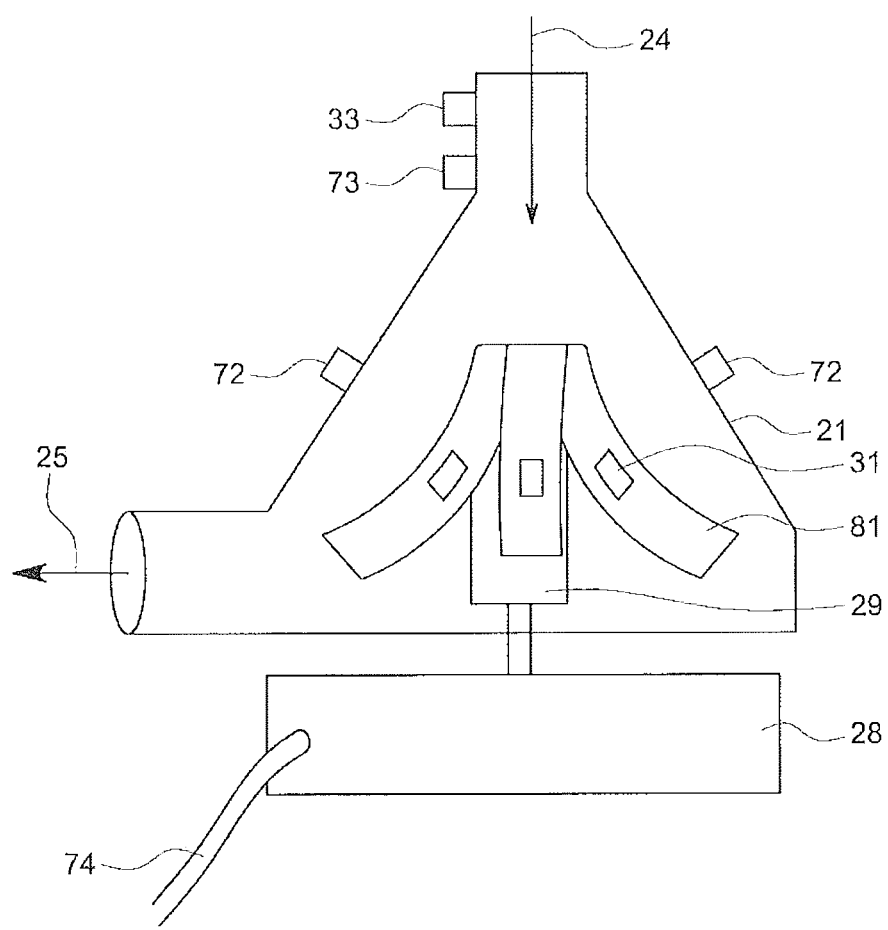
FIG. 8 depicts a cross sectional view of a blood pump according to a third preferred embodiment of the present invention.

A third embodiment of the present invention is depicted in FIG. 8, wherein a further impeller 81 has been mounted or positioned within the blood housing. The impeller 81 preferably includes at least three blades joined about a central hub. This embodiment functions in a similar manner to the blood pump in FIG. 2, wherein the elongated pivot member 29 extends in the pump housing and magnetically induces rotation of the impeller through the cooperation the first and second sets of permanent magnets.

The impeller 81 is generally conical shape wherein the blades extend radially from the hub.

Figure 9:
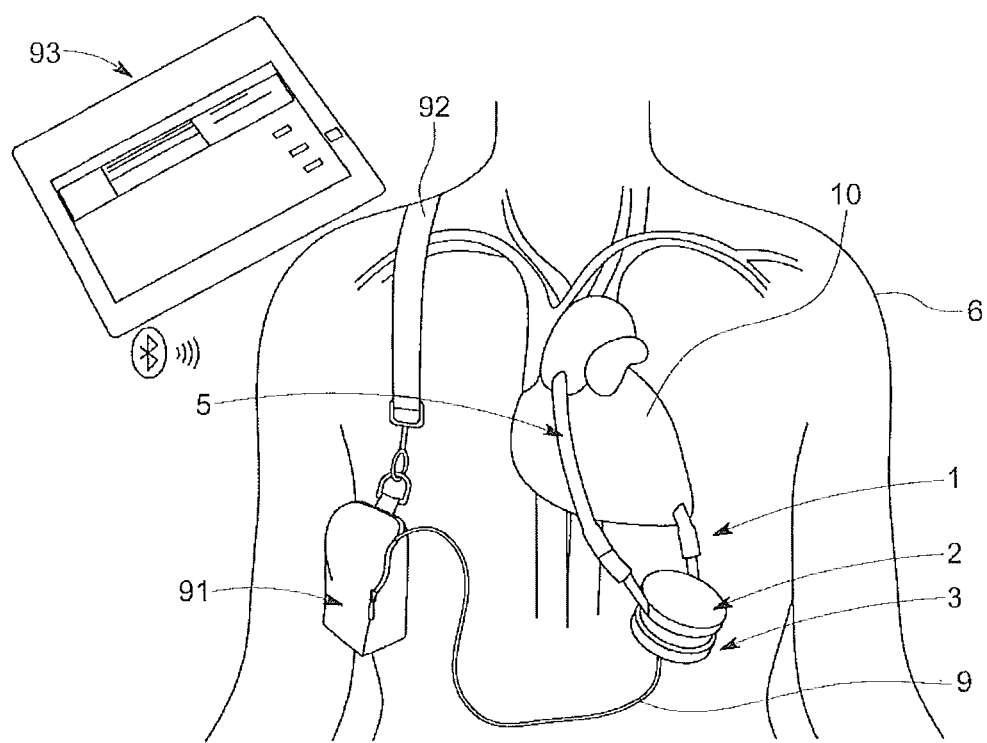
FIG. 9 depicts a schematic view of a system adapted to be part of the embodied systems.

The system shown in FIG. 9 depicts an alternate embodiment to that shown in FIG. 1. This present preferred embodiment the controller 4 and battery 4 have been replaced with a controller bag 91. The controller bag 91 preferably includes a controller with an internal rechargeable battery and an external rechargeable battery. The bag 91 is adapted to be portable and carried by the patient holding the strap 92.

The controller is adapted to communicate with the external PC or hospital monitor 93. The electrical communication may be achieved by use of Bluetooth™ or Wifi™ interfaces between the hospital monitor 93 and the controller.

Figure 10:
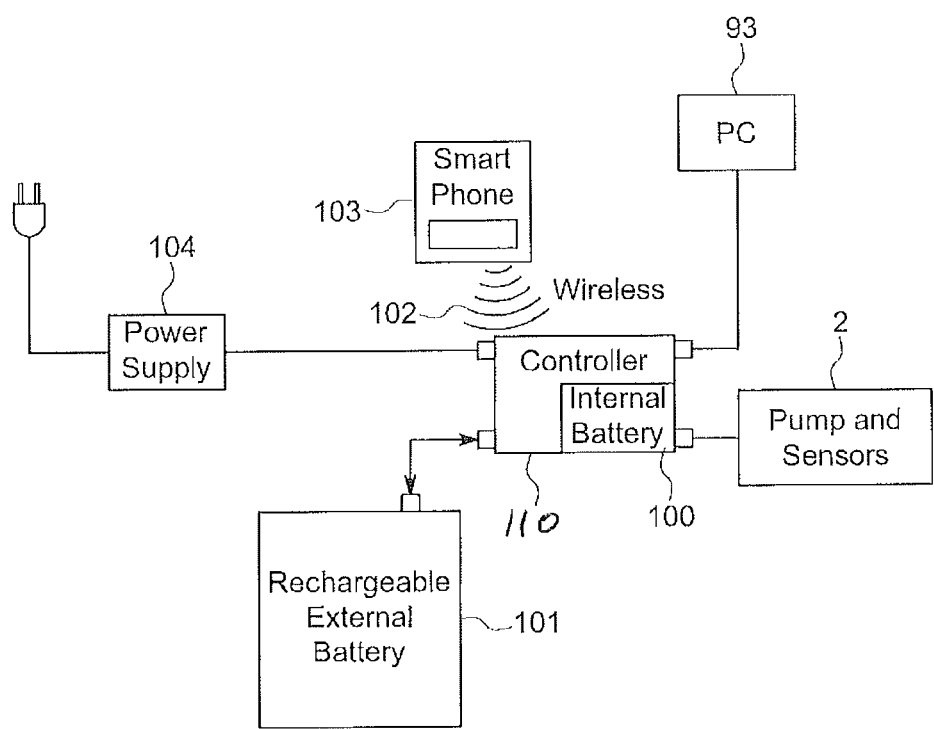
FIG. 10 depicts a schematic view of the interaction of a controller shown in FIG. 9.

FIG. 10 depicts a further schematic view of the system wherein the controller 110 includes a small internal rechargeable battery 100 which is preferably encapsulated within the same housing as the controller 110. The controller preferably is connected to the pump 2 and sensors by way a percutaneous lead. The percutaneous lead includes the wiring 74 the power the pump and electrical connections to the sensors within the blood pump.

The controller 110 may also be selectively connected to larger external rechargeable battery 101. The controller switches between the batteries 100 and 101 to maintain constant power to the pump and sensors.

The power supply 104 may be preferably a mains or AC power supply wherein the power supply 104 provides electricity to the controller and the controller redistributes the current to charge the batteries, when the power supply is connected.

Preferably, the controller may be connected by wire or wireless communication connection to a PC or hospital monitor 93. The hospital monitor 93 may be able to download results from the sensors stored within the controller or logged data relating to pump function and speed.

The hospital monitor 93 may be able to backup data from the controller 110 and also display the data in graphical format which is easier for a clinician or doctor to evaluate.

Additionally, the controller 110 may wirelessly interface 102 with other mobile electronic devices such as smart phone 103 or tablet pcs.

Figure 11:
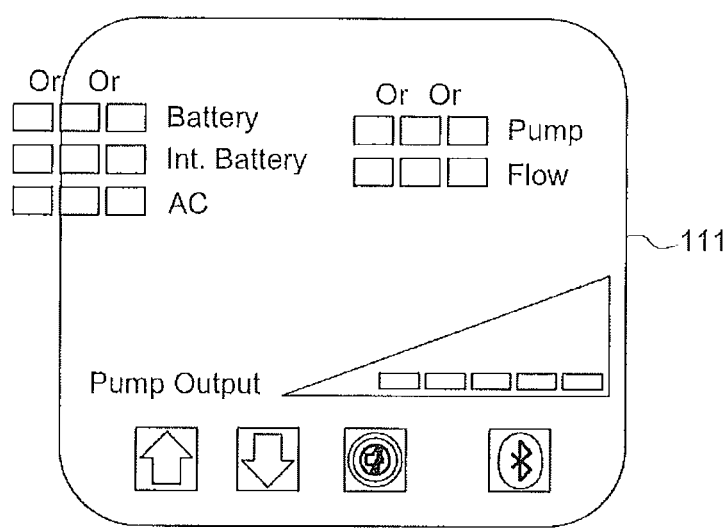
FIG. 11 depicts an example of a screen display to be used or displayed with or by the controller of FIG. 10.

FIG. 11 depicts a preferred screen layout 111 of a screen mounted on the controller 110 wherein the screen depicts to the patient, clinician, nurse or doctor basic operating details relating the pump in real time. The displayed data may include graphics depicting various statistics such as battery charge, pump flow, pump pressure, pump output, and wireless connection detection lights.

In further alternate preferred embodiments of the present invention, the pump housing and the drive unit may be external relative to the patient. Preferably, the drive unit may be secured to a belt worn by the patient. The drive unit is preferably clipped or secured the pump housing in the same or similar relationship as the earlier embodiments. The drive unit may include an additional belt securing means to releasably attached the drive unit to the belt.

Preferably, the belt may be worn around the waist of the patient and may be adjustable and/or selectively releasable depending on the circumstances. Preferably, the belt mounted configurations are well suited to being a low cost LVAD and may serve well as portable system for bridge to transplant patients.

Preferably, the inlet and outlet cannulae in this configuration may be required to exit the skin layer of the patient to allow for blood communication between the patient's circulatory system and the device. The outer surface of these cannula include a layer of textured silicone rubber to allow for tissue ingrowth and this feature may be adapted to allow the patient's natural tissue to ingrow into the outer surface of the cannula to allow for long term securing of the cannulation. The cannulae are preferably 8 to 10 mm in diameter but other diameters are also possible.

Preferably, the inlet cannula or inlet of the pump housing may include an inlet pressure sensor. The inlet pressure sensor should preferably be able to be regularly recalibrated. Preferably in some embodiments, the inlet pressure sensor may be disengaged from either the cannula or the pump housing for quick fit replacement. The inlet pressure sensor may be releasbly secured to either the pump housing or inlet cannula by a securing means. The securing means may be a Lemo™ type connector or a traditional baynet fitting or Edison screw threading attachment means wherein the sensor includes an outer sensor housing which is adapted to engage and mate with the corresponding portion of either the inlet cannula or pump housing.

Alternate embodiments may also include a simplified controller system wherein the LCD or OLED screens are replaced with one or two individual LEDs. This may reduce cost of the overall system. Further, the controller may be adapted to encode and send data transmissions to a second device (such as a smartphone) via a MODEM connected to at least one the said LEDs on the housing of the controller.

Preferably, the user or clinician may selectively sync a smartphone or similar device with the controller of the present system using an LED on the controller interacting with the camera on the smartphone when held in close proximity. Electronic messages can be encoded by the controller transmitted by light emission to the smartphone in binary and then received by the camera in the smartphone and decompressed by software running on the smartphone. Real time or logged data could be relayed to the smartphone from the system in this manner.

Further the system may also achieve the same or similar result using audio transmission sent by a speaker on or in the controller coupled to the microphone pickup of a smartphone. The method is similar to manner an acoustic coupler works.

These variants of syncing with smartphone may significantly reduce the cost of internal components of the controller as the controller no longer requires Bluetooth™ or WiFi™ capability.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

What is claimed is:
1. A centrifugal blood pump device comprising:
an impeller having a plurality of blades, the blades including blade magnets; and
a pump housing having an inlet, an outlet, a cavity, and housing magnets; and
a detachable drive unit;
wherein the inlet is for receiving blood and directing the blood onto the impeller,
wherein the impeller rotates around a central axis thereof in the cavity of the pump housing, and
wherein the impeller, in use, is suspended in the cavity by the blades which generate a centrifugal force acting on the blades in a radial direction away from the central axis and a magnetic repulsive force induced between the blade magnets of the blades and the housing magnets of the pump housing.

2. The device of claim 1, wherein the blades of the impeller extend radially away from a centre of the impeller, wherein each of the blades is embedded with one of the blade magnets, the blade magnets aligned in parallel with one another, wherein each blade magnet is oriented with a same polarity toward the detachable drive unit, and wherein the blades force blood received at the inlet through the pump housing and to the outlet.

3. The device of claim 2, wherein each of the blades is joined to an adjacent one of the blades with an elongated arm.

4. The device of claim 1, wherein the detachable drive unit engages an outer lower surface of a bottom wall of the pump housing by the magnetic force induced between the blades and the detachable drive unit.

5. The device of claim 4, wherein the detachable drive unit houses an electrical motor that drives a disc having driver magnets mounted thereon, and wherein the driver magnets are oriented with the same polarity towards the blades.

6. The device of claim 5, wherein the impeller has an upper surface of a conical profile.

7. The device of claim 4, wherein the detachable drive unit is attached to a belt adapted to be worn by the patient.

8. The device of claim 1, wherein the pump housing is integrally moulded from a polymeric substance.

9. The device of claim 1, wherein the impeller is integrally moulded from a polymeric substance.

10. The device of claim 1, wherein the impeller further has a central hub, wherein the plurality of blades comprises at least three blades joined to the central hub, wherein each of the three blades includes an upper region and a lower region, and wherein the lower region of each of the blades extends upwardly in a vertical direction and the upper region of each of the blades is deflected from a vertical axis by an angle in a direction opposed to the rotation of the impeller in use.

11. The device of claim 10, wherein the angle is between 1 to 90 degrees.

12. The device of claim 11, wherein the angle is between 10 to 45 degrees.

13. The device of claim 12, wherein each of the blades is arcuate when viewed from a top or a bottom thereof.

14. An implantable centrifugal blood pump device comprising:
    an impeller having a plurality of blades, the blades including blade magnets; and
    a pump housing having a top bezel, an upper region, a bottom wall, an inlet, an outlet, a cavity, and housing magnets positioned in the upper region; and
    a detachable drive unit;
    wherein the inlet is for receiving blood and directing the blood onto the impeller,
    wherein the impeller rotates around a central axis thereof in the cavity of the pump housing, and
    wherein the impeller, in use, is suspended in the cavity by the blades which generate a centrifugal force acting on the blades in a radial direction away from the central axis and a magnetic repulsive force induced between the blade magnets of the blades and the housing magnets of the pump housing.

15. The system of claim 14, wherein the detachable drive unit is secured against an outer surface of the bottom wall of the pump housing by a magnetic force induced between the magnets of the blades and the detachable drive unit.

16. The system of claim 15, wherein the detachable drive unit is attached to a belt adapted to be worn by the patient.

17. The device of claim 14, wherein the detachable drive unit drives a disc connected thereto, the disc includes driver magnets embedded therein, and wherein each of the blade magnets is embedded in a corresponding one of the blades.

* * * * *